US010674721B2

(12) United States Patent
Fernando et al.

(10) Patent No.: US 10,674,721 B2
(45) Date of Patent: *Jun. 9, 2020

(54) COMPOSITIONS AND METHODS FOR STABILIZING CIRCULATING TUMOR CELLS

(71) Applicant: Streck, Inc., Lavista, NE (US)

(72) Inventors: Rohan M. Fernando, Omaha, NE (US); Wayne L. Ryan, Omaha, NE (US); Brad Hunsley, Papillion, NE (US)

(73) Assignee: STRECK, INC., Lavista, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,273

(22) Filed: Oct. 5, 2018

(65) Prior Publication Data

US 2019/0075785 A1 Mar. 14, 2019

Related U.S. Application Data

(63) Continuation of application No. 14/907,167, filed as application No. PCT/US2014/047551 on Jul. 22, 2014, now Pat. No. 10,091,984.

(60) Provisional application No. 61/857,847, filed on Jul. 24, 2013.

(51) Int. Cl.
*A01N 1/02* (2006.01)
*G01N 33/574* (2006.01)

(52) U.S. Cl.
CPC ......... *A01N 1/0226* (2013.01); *G01N 33/574* (2013.01)

(58) Field of Classification Search
None
See application file for complete search history.

(56) References Cited

U.S. PATENT DOCUMENTS

| | | | |
|---|---|---|---|
| 1,432,249 A | 10/1922 | Robert | |
| 1,922,799 A | 8/1933 | Gaus | |
| 2,250,666 A | 7/1941 | Webb | |
| 2,690,624 A | 10/1954 | Phillips | |
| 2,930,570 A | 3/1960 | Leedy | |
| 3,781,120 A | 12/1973 | Engelhardt | |
| 3,867,521 A | 2/1975 | Miskel et al. | |
| 3,872,730 A | 3/1975 | Ringrose et al. | |
| 3,874,384 A | 4/1975 | Deindoerfer | |
| 3,879,295 A | 4/1975 | Glover et al. | |
| 3,973,913 A | 8/1976 | Louderback | |
| 3,994,085 A | 11/1976 | Groselak et al. | |
| 4,043,453 A | 8/1977 | Greenlee | |
| 4,318,090 A | 3/1982 | Narlow et al. | |
| 4,513,522 A | 4/1985 | Selenke | |
| 4,515,890 A | 5/1985 | Manderino et al. | |
| 4,579,759 A | 4/1986 | Breuers | |
| 4,584,219 A | 4/1986 | Baartmans | |
| 4,675,159 A | 6/1987 | Al-Sioufi | |
| 4,818,700 A | 4/1989 | Cregg et al. | |
| 4,884,827 A | 12/1989 | Kelley | |
| 4,921,277 A | 5/1990 | McDonough | |
| 5,000,484 A | 3/1991 | Phelan et al. | |
| 5,060,672 A | 10/1991 | Sandor et al. | |
| 5,110,908 A | 5/1992 | Deich et al. | |
| 5,135,125 A | 8/1992 | Andel et al. | |
| 5,196,182 A | 3/1993 | Ryan | |
| 5,213,765 A | 5/1993 | Kasai et al. | |
| 5,250,438 A | 10/1993 | Ryan | |
| 5,257,633 A | 11/1993 | Vogler et al. | |
| 5,260,048 A | 11/1993 | Ryan | |
| 5,343,647 A | 9/1994 | Bulka | |
| 5,366,249 A | 11/1994 | Diemert | |
| 5,447,842 A | 9/1995 | Simons | |
| 5,457,024 A | 10/1995 | Goldbard | |
| 5,459,073 A | 10/1995 | Ryan | |
| 5,459,253 A | 10/1995 | Wolin et al. | |
| 5,460,797 A | 10/1995 | Ryan | |
| 5,468,022 A | 11/1995 | Linder et al. | |
| 5,490,658 A | 2/1996 | Coward et al. | |
| 5,501,954 A | 3/1996 | Mahr | |
| 5,512,343 A | 4/1996 | Shaw | |
| 5,540,358 A | 7/1996 | Wiles et al. | |

(Continued)

FOREIGN PATENT DOCUMENTS

| | | |
|---|---|---|
| CA | 2406463 | 1/2001 |
| DE | 19928820 | 12/2000 |

(Continued)

OTHER PUBLICATIONS

International Search Report & Written Opinion for Application No. PCT/US2014/047551, dated Oct. 23, 2014.
Written Opinion from the European Patent Office for Application No. PCT/US2014/047551, dated Sep. 14, 2015.
International Preliminary Report on Patentability for Application No. PCT/US2014/047551, dated Dec. 10, 2015.
Rait, "Conversions of formaldehyde-modified 2'-deoxyadenosine 5'-monophosphate in conditions modeling formalin-fixed tissue dehydration" J. Histochem Cytochem 54(3): 301-10, (Mar. 1, 2006).
Lee, Thomas "Down Syndrome and Cell-Free Fetal DNA in Archived Maternal Serum" (Am J. Obstet Gynecol 2002; 187: 1217-21).
Lo et al. "Fetal Cell-Free Plasma DNA Concentrations in Maternal Blood are Stable 24 hours after" Clinical-Chemistry (Jan. 19, 2012).

(Continued)

*Primary Examiner* — Blaine Lankford
(74) *Attorney, Agent, or Firm* — The Dobrusin Law Firm, P.C.

(57) ABSTRACT

Compositions and Methods for Stabilizing Circulating Tumor Cells Methods and compositions for stabilizing a biological sample for analysis, comprising the steps of obtaining in a sample collection device a biological sample from a subject, especially blood, the biological sample including at least one circulating tumor cell from the subject. The methods may include a step of contacting the biological sample with a protective agent composition that includes a preservative agent, an optional anticoagulant, and a quenching agent to form a mixture that includes the protective agent composition and the sample.

18 Claims, 3 Drawing Sheets

(56) References Cited

U.S. PATENT DOCUMENTS

| | | |
|---|---|---|
| 5,560,657 A | 10/1996 | Morgan |
| 5,614,391 A | 3/1997 | Franciskovich et al. |
| 5,618,664 A | 4/1997 | Kiessling |
| 5,629,147 A | 5/1997 | Asgari |
| D382,343 S | 8/1997 | Wandell et al. |
| 5,654,054 A | 8/1997 | Tropsha |
| 5,688,516 A | 11/1997 | Raad |
| 5,731,156 A | 3/1998 | Golbus |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,906,744 A | 5/1999 | Carroll et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | Macfarlane |
| 6,013,240 A | 1/2000 | Behr et al. |
| 6,030,767 A | 2/2000 | Wagner |
| 6,043,032 A | 3/2000 | Yamagishi et al. |
| 6,072,086 A | 6/2000 | James et al. |
| 6,074,827 A | 6/2000 | Nelson |
| 6,077,235 A | 6/2000 | Serpentino et al. |
| 6,125,563 A | 10/2000 | Girerd |
| 6,128,840 A | 10/2000 | Boisvert |
| 6,168,922 B1 | 1/2001 | Harvey et al. |
| 6,177,163 B1 | 1/2001 | Blok et al. |
| 6,190,609 B1 | 2/2001 | Chapman |
| 6,197,539 B1 | 3/2001 | Granger |
| 6,197,540 B1 | 3/2001 | Granger |
| 6,210,889 B1 | 4/2001 | Drouin et al. |
| 6,218,531 B1 | 4/2001 | Ekenberg |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,527,242 B1 | 3/2003 | Kennedy |
| 6,527,957 B1 | 3/2003 | Deniega |
| 6,551,267 B1 | 4/2003 | Cohen et al. |
| 6,560,847 B2 | 5/2003 | Ohlsson |
| 6,579,672 B1 | 6/2003 | Granger |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski et al. |
| 6,821,789 B2 | 11/2004 | Augello et al. |
| 6,860,513 B2 | 3/2005 | Kaufman |
| 6,884,573 B2 | 4/2005 | Fischer |
| 6,916,634 B2 | 7/2005 | Kopreski |
| 6,939,671 B2 | 9/2005 | Kopreski |
| 6,994,790 B2 | 2/2006 | Corbin |
| 7,022,478 B2 | 4/2006 | Rainer et al. |
| 7,044,941 B2 | 5/2006 | Mathias |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern |
| 7,332,277 B2 | 2/2008 | Dhallan |
| 7,332,288 B2 | 2/2008 | Terstappen et al. |
| 7,358,039 B2 | 4/2008 | Fischer |
| 7,390,663 B2 | 6/2008 | Ryan et al. |
| 7,398,999 B2 | 7/2008 | Kaufman |
| 7,419,832 B2 | 9/2008 | Hunsley |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,767,460 B2 | 8/2010 | Hunsley et al. |
| 8,841,077 B2 | 9/2014 | Paige |
| 9,040,255 B2 | 5/2015 | Tsinberg |
| 9,120,849 B2 | 9/2015 | Chiklis et al. |
| 9,127,048 B2 | 9/2015 | Chiklis et al. |
| 10,091,984 B2* | 10/2018 | Fernando ............. G01N 33/574 |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | DeLaCruz |
| 2002/0086346 A1 | 7/2002 | Ryan |
| 2002/0119503 A1 | 8/2002 | Ryan et al. |
| 2003/0232377 A1 | 12/2003 | Thomas |
| 2004/0014107 A1 | 1/2004 | Garcia-Blanco |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0232377 A1 | 3/2005 | Paterlini-Brechot |
| 2005/0107316 A1 | 5/2005 | Strebhardt et al. |
| 2005/0181353 A1 | 8/2005 | Rao et al. |
| 2005/0181463 A1 | 8/2005 | Rao et al. |
| 2005/0277204 A1 | 12/2005 | Hollis et al. |
| 2006/0008807 A1 | 1/2006 | O'Hara |
| 2006/0105372 A1 | 5/2006 | Bair et al. |
| 2006/0194192 A1 | 8/2006 | Rao et al. |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan |
| 2007/0202525 A1 | 8/2007 | Quake et al. |
| 2007/0243548 A1 | 10/2007 | Bischoff |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson |
| 2008/0108071 A1 | 5/2008 | Thompson |
| 2008/0119645 A1 | 5/2008 | Griffey et al. |
| 2008/0206866 A1 | 8/2008 | Zieglschmid et al. |
| 2008/0261292 A1 | 10/2008 | Kopreski |
| 2008/0318801 A1 | 12/2008 | Leung et al. |
| 2009/0034446 A1 | 2/2009 | Adams et al. |
| 2009/0081678 A1 | 3/2009 | Ryan et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0190796 A1 | 7/2010 | Verkman |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0027771 A1 | 2/2011 | Deng |
| 2011/0053208 A1 | 3/2011 | Reiss |
| 2011/0111410 A1 | 5/2011 | Ryan et al. |
| 2012/0164676 A1 | 6/2012 | Tsinberg |
| 2012/0308990 A1 | 12/2012 | TerMaat |
| 2013/0034860 A1 | 2/2013 | Fernando |
| 2014/0054508 A1 | 2/2014 | Fernando |
| 2014/0080112 A1 | 3/2014 | Ryan |
| 2014/0199681 A1 | 7/2014 | Ryan |
| 2015/0301037 A1 | 10/2015 | Tsinberg et al. |
| 2016/0143268 A1 | 5/2016 | Ryan |

FOREIGN PATENT DOCUMENTS

| | | |
|---|---|---|
| EP | 1031626 A1 | 8/2000 |
| EP | 1207208 A2 | 5/2002 |
| EP | 1217372 A1 | 6/2002 |
| EP | 1816461 A1 | 8/2007 |
| EP | 1889921 A2 | 2/2008 |
| EP | 1425294 B1 | 7/2008 |
| EP | 2228453 A1 | 9/2010 |

(56) References Cited

FOREIGN PATENT DOCUMENTS

| | | |
|---|---|---|
| EP | 2216416 | 11/2010 |
| EP | 2674502 A1 | 12/2013 |
| EP | 2411808 B1 | 11/2015 |
| WO | 93/05650 | 4/1993 |
| WO | 94/02646 | 2/1994 |
| WO | 95/26417 | 10/1995 |
| WO | 98/02528 A1 | 1/1998 |
| WO | 98/02740 A1 | 1/1998 |
| WO | 98/59042 A1 | 12/1998 |
| WO | 00/06780 A1 | 2/2000 |
| WO | 00/75647 | 12/2000 |
| WO | 00/77235 | 12/2000 |
| WO | 01/79851 | 10/2001 |
| WO | 01/98542 | 12/2001 |
| WO | 02/055985 | 7/2002 |
| WO | 03/018757 A2 | 3/2003 |
| WO | 03/019141 A2 | 6/2003 |
| WO | 03/069344 | 8/2003 |
| WO | 03/095974 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | 2010/096323 A1 | 8/2010 |
| WO | 2010/123908 A1 | 10/2010 |
| WO | 2011/014741 A1 | 2/2011 |
| WO | 2011/057184 | 5/2011 |
| WO | 2011/082415 A2 | 7/2011 |
| WO | 2012/145662 A1 | 10/2012 |
| WO | 2012/166913 A1 | 12/2012 |
| WO | 2013/086428 A1 | 6/2013 |
| WO | 2013/123030 A2 | 8/2013 |
| WO | 2014/029791 A1 | 2/2014 |

OTHER PUBLICATIONS

Lo, Y M Dennis, "Fetal Nucleic Acids in Maternal Plasma, Toward the Development of Noninvasive Prenatal Diagnosis of Fetal Chromosomal Aneuploidies," 2008 New York Academy of Sciences.
Wagner, J, "Free DNA—new potential analyte in clinical laboratory diagnostics?" Biochem Med (Zagreb) 22(1): 24-38, 2006.
Dhallan et al., "Methods to Increase the Percentage of Free Fetal DNA Recovered from the Maternal Circulation," JAMA 291, 1114-1119, Mar. 3, 2004.
Chinnapapagari et al., "Treatment of Material Blood Samples with Formaldehyde does not alter the Proportion of Circulatory Fetal Nucleic Acids (DNA and mRNA) in Maternal Plasma", Technical Briefs, University Women's Hospital/Dept. of Research, Basel, Switzerland, pp. 652-655, 1005.
A Sample Preparation and Analysis System for Indentification of Circulating Tumor Cells; vol. 25, No. 1; Spring 2002; Journal of Clinical Ligand Assay.
Bianchi et al., "PCR Quantification of Fetal Cells in Maternal Blood in Normal and Aneuploid Pregnancies" Am J. Hum. Genet. 61:822-829, 1997.
American Association for Cancer Research; 93ra Annual Meeting; Apr. 6-10, 2002; San Francisco, California; vol. 43, Mar. 2002.
Annals of the New York Academy of Sciences: Circulating Nucleic Acids in Plasma or Serum II, vol. 945, Issue pp. 1-291 (Sep. 2001).
Ashoor, G et al., "Trisomy 13 detection in the first trimester of pregnancy using a chromosome-selective cell-free DNA analysis method" Ultrasound in Obstetrics & Gynecology; 41(1):21-5, Nov. 23, 2012.
Barrett et al., "Implementing Prenatal Diagnosis Based on Cell-Free Fetal DNA: Accurate Identification of Factors Affecting Fetal DNA Yield," PLoS One, 6(10):e25202, Oct. 4, 2011.
Bayindir, B et al., "Noninvasive Prenatal Testing Using a Novel Analysis Pipeline to Screen for All Autosomal Fetal Aneuploidies Improves Pregnancy Management," European Journal of Human Genetics. Jan. 14, 2015.
Beck; J et al., Digital Droplet PCR for Rapid Quantification of Donor DNA in the Circulation of Transplant Recipients as a Potential Universal Biomarker of Graft Injury. Clinical chemistry; 59(12):1732-41, Dec. 1, 2013.
Benachi, A et al., Cell-Free DNA Analysis in Maternal Plasma in Cases of Fetal Abnormalities Detected on Ultrasound Examination. Obstetrics & Gynecology; 125(6):1330-7, Jun. 1, 2015.
Bethel, K et al., "Fluid phase biopsy for detection and characterization of circulating endothelial cells in myocardial infarction," Physical biology; 11(1):016002, Feb. 1, 2014.
Bevilacqua, E et al., "Performance of screening for aneuploidies by cell-free DNA analysis of maternal blood in twin pregnancies," Ultrasound in Obstetrics & Gynecology; 45(1):61-6, Jan. 1, 2015.
Bianchi, DW et al., "DNA sequencing versus standard prenatal aneuploidy screening" New England Journal of Medicine;370(9):799-808, Feb. 27, 2014.
Bianchi, D et al., "Fetal sex chromosome testing by maternal plasma DNA sequencing: clinical laboratory experience and biology," Obstetrics & Gynecology; 125(2):375-82, Feb. 1, 2015.
Bianchi, "invited Editorial Fetal DNA in Maternal Plasma: The Plot Thickens and the Placental Barrier Thins," The American Society of Human Genetics, 62:763-764, 1998.
Bina-Stein, et al., Aurintricarboxylic Acid Is a Nonspecific Enzyme Inhibitor, Department of Chemistry, Yale University, New Haven, Connecticut. 1975, 12:191-193.
Biocept—Expands Patent Protection for Liquid Biopsy Platform dated Jun. 1, 2015; http://ir.biocept.com/releasedetail.cfm?releaseID=915635.
Biocept (BIOC) Announces Pattent for Blood Collection and Transport Tube; StreetInsider.com; http://www.streetinsider.com/corporate+news/biocept+(BIOC)+Armounces; Jun. 1, 2015.
Bioreceptor Fenofluids: Novel Characteristics and their Utility in Medical Applications; P. A. Liberti, J. N. Chiarappa, A. C. Hovespian, C. G. Rao; Supplied by the British Library; 1996 Kluwer Academic Publishers.
Brar, H et al., "The fetal fraction ot cell-free DNA in maternal plasma is not affected by a priori risk of fetal trisomy," The Journal of Maternal-Fetal & Neonatal Medicine; 26(2):143-5, Jan. 1, 2013.
Bruno, D et al., Use of copy number deletion polymorphisms to assess DNA chimerism. Clinical chemistry; 60(8):1105-14, Aug. 1, 2014.
Buysse, K et al. "Reliable noninvasive prenatal testing by massively parallel sequencing of circulating cell-free DNA from maternal plasma processed up to 24h after venipuncture," Clinical biochemistry, 46(18 ):1783-6, Dec. 31, 2013.
Carlsson A et al., "Circulating Tumor Microemboli Diagnostics for Patients with Non-Small-Cell Lung Cancer," Journal of Thoracic Oncology; 9(8):1111-9, Aug. 1, 2014.
Chan et al, "Hypermethylated RASSFIA in maternal Plasma: A Universal Fetal DNA Marker that improves the Reliability of Noninvasive Prenatal Diagnosis," Clinical Chemistry, 2211-2218, 52(12), 2006.
Chudziak, J et al., "Clinical evaluation of a novel microfluidic device for epitope-independent enrichment of circulating tumour cells in patients with small cell lung cancer," The Analyst;141(2):669-78, Nov. 2015.
Lo, Y M Dennis"Circulating Nucleic Acids in Plasma and Serum: An Overview", (2001).
Clark-Ganheart et al., "Use of Cell-Free DNA in the Investigation of Intrauterine Fetal Demise and Miscarriage," Obstetrics & Gynecology; 125(6):1321-9, Jun. 1, 2015.
Zhang, Yi et al., "Effect of Formaldehyde Treatment on the recovery of cell-free fetal DNA from Maternal Plasma at Different Processing Times" Clinic Chimica Acta 397, 60-64, 2008.
Clinical Applications of Flow Cytometry: Immunophenotyping of Leukemic Cells; Approved Guideline; Jun. 1998; vol. 18 No. 8; NCCLS.
Lo, et al., "Increased Fetal DNA Concentrations in the Plasma of Pregnant Women Carrying Fetuses with Trisomy 21" Clinical Chemistry 45:10, 1747-1751 (1999).
Lo, Y M Dennis "Molecular Testing of Urine: Catching DNA on the way out" Clinical Chemistry 46, No. 8, 2000.

(56) References Cited

OTHER PUBLICATIONS

Botezatu et al. "Genetic Analysis of DNA Excreted in Urine: A New Approach for Detecting Specific Genomic DNA Sequences from Cells Dying in an Organism" Clinical Chemistry 46:8, 1078-1084 (2000).
Chiu, Rosa et al., "Effects of Blood-Processing Protocols on Fetal and Total DNA Quantification in Maternal Plasma," Clinical Chemistry 47:9, 1607-1613, 2001.
Chung et al., "Lack of Dramatic Enrichment of Fetal DNA in Maternal Plasma by Formaldehyde Treatment," Clinical Chemistry, 51, No. 3, 2005.
Comas, C et al., "initial Experience with Non-Invasive Prenatal Testing of Cell-Free DNA for Major Chromosomal Anomalies in a Clinical Setting," The Journal of Maternal-Fetal & Neonatal Medicine; (0):1-6, Aug. 12, 2014.
Curnow et al., "Detection of Triploid, Molar, and Vanishing Twin Pregnancies by a Single-Nucleotide Polymorphism—Based Noninvasive Prenatal Test," American Journal of Obstetrics and Gynecology; 212(1):79-e1 Jan. 2015.
Dash et al. "Using Noninvasive Prenatal Testing for Aneuploidies in a Developing Country: Lessons Learnt" Journal of Fetal Medicine, 1(3):131-5, 2014.
Denis et al. "Efficient Detection of BRAF Mutation in Plasma of Patients after Long-term Storage of Blood in Cell-Free DNA Blood Collection Tubes" Clinical Chemistry, 61(6):886-8, Jun. 1, 2015.
Chung et al.; "Detrimental Effect of Formaldehyde on Plasma RNA Detection" 51 (6): 10, Jul. 12, 2010.
Dharajiya et al. "Noninvasive Prenatal Testing Using Cell-Free Fetal DNA in Maternal Plasma" Current Protocols in Human Genetics, 8-15, Jan. 20, 2015.
Diamond et al. "Diverse and Targetable Kinase Alterations Drive Histiocytic Neoplasms" Cancer discovery: CD-15, Nov. 15, 2015.
Ding, et al., MS Analysis of Single-Nucleotide Differences in Circulating Nucleic Acids: Application to Noninvasive Prenatal Diagnosis, 101:10762-10767, 2004.
Fairbrother et al. "Clinical experience of noninvasive prenatal testing with cell-free DNA for fetal trisomies 21, 18, and 13, in a general screening population" Prenatal Diagnosis; 33(6):580-3, Jun. 1, 2013.
Futch et al. "Initial clinical laboratory experience in noninvasive prenatal testing for fetal aneuploidy from maternal plasma DNA samples" Prenatal Diagnosis; 33(6):569-74, Jun. 1, 2013.
Gil et al. "Cell-free DNA analysis for trisomy risk assessment in first-trimester twin pregnancies" Fetal Diagnosis and Therapy; 35(3):204-11, Nov. 15, 2013.
Gil et al. "UK NHS pilot study on cell-free DNA testing in screening for fetal trisomies: factors affecting uptake" Ultrasound in Obstetrics & Gynecology; 45(1):67-73. Jan. 1, 2015.
Gil et al. "implementation of maternal blood cell-free DNA testing in early screening for aneuploidies" Ultrasound in Obstetrics & Gynecology; 42(1):34-40, Jun. 7, 2013.
Gonzalez, et al., "Application of Fetal DNA Detection in Maternal Plasma: A Prenatal Diagnosis Unit Experience," Journal of Histochemistry & Cytochemistry, 53(3): 307-314, 2005.
Grömminger et al. "Fetal aneuploidy detection by cell-free DNA sequencing for multiple pregnancies and quality issues with vanishing twins" Journal of Clinical Medicine: 3(3):679-92, Jun. 25, 2014.
Gross et al. "Rapid changes in circulating tumor cells following anti-angiogenic therapy" Convergent Science Physical Oncology; 1(1):015002, Sep. 15, 2015.
Hidestrand et al. "Influence of temperature during transportation on cell-free DNA analysis" Fetal diagnosis and Therapy; 31(2):122-8, 2012.
Hindson et al. "High-throughput droplet digital PCR system for absolute quantitation of DNA copy number" Analytical Chemistry; 83(22):8604-10, Oct. 28, 2011.
Holford et al, "Stability of beta-actin mRNA in plasma," Annals of the New York Academy of Science, 108-111, 1137, Aug. 2008.
Holmberg et al. "Akonni TinTip® and Qiagen® methods for extraction of fetal circulating DNA—evaluation by real-time and digital PCR." PloS One; 8(8):e73068, Aug. 2013.
Hooks et al, "Non-invasive risk assessment of fetal sex chromosome aneuploidy through directed analysis and incorporation of fetal fraction" Prenatal Diagnosis; 34(5):496-9, May 2014.
http://ir.biocept.com/secfiling.cfm?filingid=1193125-15-16425&cik=1044378; Biocept Completing the Answer; Jan. 21, 2015.
Hynek et al, "MoM-based Approach to Noninvasive Prenatal Testing Using Exponentially Weighted Moving Average Chart and Chromosomal Fingerprint" International Journal of Biomedicine and Healthcare. 12, 2015.
Ignatiadis et al. "Circulating Tumor Cells and Circulating Tumor DNA: Challenges and Opportunities on the Path to Clinical Utility" Clinical Cancer Research; 21 (21): 4786-800, Nov. 2015.
Jensen et al. "High-throughput massively parallel sequencing for fetal aneuploidy detection from maternal plasma" PloS One; 8(3): e57381, Mar. 2013.
Jeon et al. "The feasibility study of non-invasivetal trisomy 18 and 21 detection with semiconductor sequencing platform" PLoS One; 9(10):e110240, Oct. 20, 2014.
Juneau et al. "Microarray-based cell-free DNA analysis improves noninvasive prenatal testing" Fetal Diagnosis and Therapy; 36(4):282-6, 2014.
Kadam et al. "Quantitative measurement of cell-free plasma DNA and applications fbr detecting tumor genetic variation and promoter methylation in a clinical setting" The Journal of Molecular Diagnostics. Jul. 31, 2012;14(4):346-56.
Katz et al. No Date. "Mass-Volume Equivalents of Common Chemical Solids." Available at <http://www.chymist.com/Mass-volume%20equivalents.pdf>. Accessed Oct. 22, 2015. 4 pages.
Kidess et al. "Mutation profiling of tumor DNA from plasma and tumor tissue of colorectal cancer patients with a novel, high-sensitivity multiplexed mutation detection platform" Oncotarget. Feb. 2015; 6(4):2549.
Kirkizlar et al. "Detection of Clonal and Subclonal Copy-Number Variants in Cell-Free DNA from Patients with Breast Cancer Using a Massively Multiplexed PCR Methodology" Translational oncology. Oct. 31, 2015;8(5):407-16.
Kwee et al. "Measurement of Circulating Cell-Free DNA in Relation to 18F-Fluorocholine PET/CT Imaging in Chemotherapy—Treated Advanced Prostate Cancer" Clinical and Translational Science. Feb. 1, 2012;5(1):65-70.
Lambert-Messerlian et al. "Feasibility of using plasma rather than serum in first and second trimester multiple marker Down's syndrome screening. Journal of medical screening" Dec. 1, 2012;19(4):164-70.
Lanman et al.. "Analytical and clinical validation of a digital sequencing panel for quantitative, highly accurate evaluation of cell-free circulating tumor DNA" PloS one. Oct. 16, 2015;10(10):e0140712.
Lee et al., "Survival of Donor Leukocyte Subpopulations in Immunocompetent Transfusion Recipients: Frequent Long-Term Microchimerism in Severe Trauma Patients," Blood, 3127-3139, 93, 1999.
Lee et al. "Performance of Momguard, a new non-invasive prenatal testing protocol developed in Korea" Obstetrics & Gynecology Science, Sep. 1, 2015;58(5):340-5.
Li, et al., "Detection of Paternally Inherited Fetal Point Mutations for β-Thalassemia Using Size-Fractionated Cell-Free DNA in Maternal Plasma," available at: www.jama.com, 293:843-849, 2005.
Liao et al. "Noninvasive prenatal diagnosis of common aneuploidies by semiconductor sequencing" Proceedings of the National Academy of Sciences. May 20, 2014;111(20):7415-20.
Liu et al. "Placental mosaicism for Trisomy 13: a challenge in providing the cell-free fetal DNA testing" Journal of assisted reproduction and genetics. May 1, 2014;31(5):589-94.
Lo et al., "Noninvasive prenatal diagnosis for fetal chromosomal aneuploidies by maternal plasma nucleic acid analysis" Clinical Chemistry, American Association for Clinical Chemistry, Washington DC Lnkd—Doi:10.1373/Clinchem.2007.100016, vol. 54, No. 3, pp. 461-466, Jan. 17, 2008.

(56) References Cited

OTHER PUBLICATIONS

Lo, et al., "Quantitative Analysis of Fetal DNA in Maternal Plasma and Serum: Implications for Noninvasive Prenatal Diagnosis," by The American Society of Human Genetics, 62:768-775, 1998.
Lo, "Fetal DNA in Maternal Plasma: Biology and Diagnostic Applications," Clinical Chemistry 46:12 1903-1906, 2000.
Lu et al. Detection and Characterization of Circulating Tumour Cells from Frozen Peripheral Blood Mononuclear Cells. Journal of Circulating Biomarker. Dec. 1, 2015;35(12):1243-6.
Machaca et al., "Characterization of apoptosis-like endonuclease activity in avian thymocytes," Biology of the Cell, 15-22, 76(1), Elsevier, Paris France, Jan. 1, 1992.
Madabusi et al., "RNA extraction for Arrays," Methods in Enzymology, 1-14, 411, 2006.
McCullough et al. "Non-invasive prenatal chromosomal aneuploidy testing-clinical experience: 100,000 clinical samples" PLoS One, Oct. 7, 2014;9(10):e109173.
Nair et al. "An observational study of circulating tumor cells and (18) F-FDG PET uptake in patients with treatment-naive non-small cell lung cancer" PloS One. Jul. 5, 2013;8(7);e67733.
Nicolaides et al. "Validation of targeted sequencing of single-nucleotide polymorphisms for non-invasive prenatal detection of aneuploidy of chromosomes 13, 18, 21, X, and Y" Prenatal Diagnosis, Jun. 1, 2013;33(6):575-9.
Norton et al. "Non-Invasive Chromosomal Evaluation (NICE) Study: results of a multicenter prospective cohort study for detection of fetal trisomy 21 and trisomy 18" American journal of Obstetrics and Gynecology, Aug. 31, 2012;207(2):137-e1.
Norton et al. "Cell-free DNA analysis for noninvasive examination of trisomy" New England Journal of Medicine. Apr. 23, 2015;372(17):1589-97.
Ono et al. "Circulating microRNA Biomarkers as Liquid Biopsy for Cancer Patients: Pros and Cons of Current Assays" Journal of clinical medicine. Oct. 23, 2015;4(10):1890-907.
Palmer et al., "Flow cytometric determination of residual white blood cell levels in preserved samples from leukoreduced blood products," Transfusion, 118-128, 48(1), Jan. 2008.
Pan, et al., "Cell-free Fetal DNA Levels in Pregnancies Conceived by IVF", Human Reproduction, 20(11):3152-3156, 2005.
Persico et al. "Cell-free DNA testing in the maternal blood in high-risk pregnancies after first trimester combined screening" Prenatal Diagnosis. Jan. 1, 2016.
Pertl, et al., "Fetal DNA in Maternal Plasma: Emerging Clinical Applications," by the American College of Obstetricians and Gynecologists, 98:483-490, 2001.
Pinzani et al., "Circulating Nucleic Acids in Cancer and Pregnancy," Methods: A Companion to Methods in Enzymology, 302-307, 40 (4), Academic Press Inc., New York Apr. 1, 2010.
Sekizawa et al.; "Apoptosis in Fetal Nucleated Erythrocytes Circulating in Maternal Blood" Prenatal Diagnosis; 20: 886-889, 2000.
Punnoose et al. "PTEN loss in circulating tumour cells correlates with PTEN loss in fresh tumour tissue from castration-resistant prostate cancer patients" British Journal of Cancer. Oct. 20, 2015;113(8):1225-33.
Puren et al., Laboratory operations, specimen processing, and handling for viral load testing and surveillance, Journal of Infectious Diseases, S27-S36, 201(supp 1), University of Chicago Press, Chicago II, Apr. 15, 2010.
Quezada et al. "Fetal fraction of cell-free DNA in maternal plasma in the prediction of spontaneous preterm delivery." Ultrasound in Obstetrics & Gynecology. Jan. 1, 2015;45(1):101-5.
Quezada et al. "Screening for trisomies 21, 18 and 13 by cell-free DNA analysis of maternal blood at 10-11 weeks' gestation and the combined test at 11-13 weeks" Ultrasound in Obstetrics & Gynecology. Jan. 1, 2015;45(1):36-41.
Risberg B. "Establishment of PCR based methods for detection of ctDNA in blood." Thesis submitted for the Master's degree in Biomedicine. Oslo University Hospital, Institute for Cancer Research, Department of Genetics and Oslo and Akershus University College of Applied Sciences. May 5, 2013.
Ruiz et al. "Limited genomic heterogeneity of circulating melanoma cells in advanced stage patients" Physical Biology. Feb. 1, 2015;12(1):016008.
Salvianti et al. "Single circulating tumor cell sequencing as an advanced tool in cancer management" Expert review of molecular diagnostics. Nov. 27, 2015:1-3.
Samango-Sprouse et al. "SNP-based non-invasive prenatal testing detects sex chromosome aneuploidies with high accuracy" Prenatal diagnosis. Jul. 1, 2013;33(7):643-9.
Samoila et al. "Method development and validation for clinical cfDNA extraction from blood" InASCO Annual Meeting Proceedings May 20, 2015 (vol. 33, No. 15_suppl, p. e22185).
Samuel et al. "The effect of chorionic villus sampling on the fraction of cell-free fetal DNA in maternal plasma" The Journal of Maternal-Fetal & Neonatal Medicine. Oct. 15, 2015:1-4.
Scheffer et al. "Noninvasive fetal blood group genotyping of rhesus D, c, E and of K in alloimmunised pregnant women: evaluation of a 7-year clinical experience" BJOG: An International Journal of Obstetrics & Gynaecology. Oct. 1, 2011;118(11):1340-8.
Schiavon et al. "Analysis of ESR1 mutation in circulating tumor DNA demonstrates evolution during therapy for metastatic breast cancer" Science translational medicine. Nov. 11, 2015; 7(313):313ra182-.
Seo et al. "An Experience of Using the Harmony Test for Genomics-Based Non-Invasive Prenatal Testing" Journal of Laboratory Medicine and Quality Assurance. Mar. 1, 2015;37(1):44-6.
Shi et al. "Feasibility of noninvasive prenatal testing for common fetal aneuploidies in an early gestational window" Clinica Chimica Acta. Jan. 15, 2015;439:24-8.
Sigma-Aldrich. "1-Aza-3,7-dioxabicyclo[3.3.0]octane-5-methanol solution." Available online at www.sigmaaldrich.com/catalog/product/aldrich/417807?lang=en&region=US. 5 pages. Accessed Jan. 1, 2014.
Sillence et al. "Fetal Sex and RHD Genotyping with Digital PCR Demonstrates Greater Sensitivity than Real-time PCR" Clinical Chemistry. Nov. 1, 2015;61(11):1399-407.
Smid et al., "Quantitative Analysis of Fetal DNA in Maternal Plasma in Pathological Conditions Associated with Placental Abnormalities," Annals New York Academy of Sciences, 951:133-137, 2001.
Song et al. "Non-invasive prenatal testing for fetal aneuploidies in the first trimester of pregnancy" Ultrasound in Obstetrics & Gynecology. Jan. 1, 2015;45(1):55-60.
Sparks et al. "Noninvasive prenatal detection and selective analysis of cell-free DNA obtained from maternal blood: evaluation for trisomy 21 and trisomy 18" American Journal of Obstetrics and Gynecology. Apr. 30, 2012;206(4):319-e1.
Sparks et al. "Selective analysis of cell-free DNA in maternal blood for evaluation of fetal trisomy" Prenatal Diagnosis, Jan. 1, 2012;32(1):3-9.
Stokowski et al. "Clinical performance of non-invasive prenatal testing (NIPT) using targeted cell-free DNA analysis in maternal plasma with microarrays or next generation sequencing (NGS) is consistent across multiple controlled clinical studies" Prenatal Diagnosis. Dec. 1, 2015;35(12):1243-6.
Stumm et al. "Diagnostic accuracy of random massively parallel sequencing for non-invasive prenatal detection of common autosomal aneuploidies: a collaborative study in Europe" Prenatal Diagnosis. Feb. 1, 2014;34(2):185-91.
Takabayashi et al. "Development of Non-invasive Fetal DNA Diagnosis from Maternal Blood," Prenatal Diagnosis, 15:74-77, 1995.
Smid et al., "Evaluation of Different Approaches for Fetal DNA Analysis from Maternal Plasma and Nucleated Blood Cells", Technical Briefs, pp. 1570-1572, 1999.
Thung et al. "Implementation of whole genome massively parallel sequencing for noninvasive prenatal testing in laboratories" Expert Review of Molecular Diagnostics. Jan. 2, 2015;15(1):111-24.
Toro. "Detection of PIK3CA Mutations in Plasma Tumor DNA Circulating in Peripheral Blood of Breast Cancer Patients" Thesis submitted for the degree of Master of Science in Molecular and Cellular Biology. Johns Hopkins University, Baltimore, Maryland, Apr. 2014.

(56) References Cited

OTHER PUBLICATIONS

Toro et al. "Comparison of cell stabilizing blood collection tubes for circulating plasma tumor DNA" Clinical Biochemistry. Oct. 31, 2015;48(15):993-8.
Tynan et al. Application of risk score analysis to low-coverage whole genome sequencing data for the noninvasive detection of trisomy 21, trisomy 18, and trisomy 13. Prenatal diagnosis. Jan. 1, 2015.
US Food and Drug Administration, "Draft Guidance for Industry: Pre-Storage Leukocyte Reduction of Whole Blood and Blood Components Intended for Transfusion, Vaccines." Blood & Biologics, available at: www.fda.gov/biologicsbloodvaccines/guidance complianceregillatoryinformation/guidances/blood/ucm076769. htm, last accessed Apr. 13, 2011.
Vandenberghe et al. "Non-invasive detection of genomic imbalances in Hodgkin/Reed-Sternberg cells in early and advanced stage Hodgkin's lymphoma by sequencing of circulating cell-free DNA: a technical proof-of-principle study" The Lancet Haematology, Feb. 28, 2015;2(2):e55-65.
Verweij et al. "European Non-Invasive Trisomy Evaluation (EU-NITS) study: a multicenter prospective cohort study for non-invasive fetal trisomy 21 testing" Prenatal Diagnosis, Oct. 1, 2013;33(10):996-1001.
Wang D et al. Exploring Glycan Markers for Immunotyping and Precision-targeting of Breast Circulating Tumor Cells. Archives of medical research. Dec. 1, 2015.
Wang E et al. "Gestational age and maternal weight effects on fetal cell-free DNA in maternal plasma" Prenatal diagnosis. Jul. 1, 2013;33(7):662-6.
Wang P et al. "Sensitive detection of mono-and polyclonal ESR1 mutations in primary tumors, metastatic lesions and cell free DNA of breast cancer patients" Clinical Cancer Research. Oct. 23, 2015;clincanres-1534.
Wang Q et al. "Real-time PCR evaluation of cell-free DNA subjected to various storage and shipping conditions" Genetics and Molecular Research. Jan. 1, 2015;14(4):12797-804.
Wang Y et al. "Maternal mosaicism is a significant contributor to discordant sex chromosomal aneuploidies associated with noninvasive prenatal testing" Clinical chemistry. Jan. 1, 2014;60(1):251-9.
Werner et al. "Analytical Validation and Capabilities of the Epic CTC Platform: Enrichment-Free Circulating Tumour Cell Detection and Characterization" Journal of Circulating Biomarkers. 2015 4:3.
Wienzek-Lischka et al. "Noninvasive fetal genotyping of human platelet antigen-1a using targeted massively parallel sequencing" Transfusion Apr. 1, 2015.
Willems et al. "The first 3,000 non-invasive prenatal tests (NIPT) with the harmony test in Belgium and the Netherlands" Facts, Views & Vision in ObGyn. 2014;6(1):7.
Wong et al. "Optimizing blood collection, transport and storage conditions for cell free DNA increases access to prenatal testing" Clinical Biochemistry. Aug. 31, 2013;46(12):1099-104.
Woolcock et al. "Noninvasive prenatal testing." Australian Family Physician. Jul. 1, 2014;43(7):432.
Lo et al. "Presence of Fetal DNA in Maternal Plasma and Serum" The Lancet, 350, 485-87, 1997.
Zill et al. "Cell-free DNA next-generation sequencing in pancreatobiliary carcinomas" Cancer discovery. Oct. 1, 2015;5(10):1040-8.
European Communication dated May 25, 2016; Application No. 13706856.5.
European Office Action, Application No. 13706856.5 dated Mar. 10, 2016.
European Office Action for Application No. 13706856.5 dated May 27, 2015.
European Patent Office Summons to Attend dated Jan. 27, 2016 for Application No. 10704474.5.
European Office Action dated Nov. 17, 2014 for Application No. 10704474.5.
European Communication dated Aug. 30, 2016 for Application No. 10704474.5.
Wiebe et al., "Inhibition of Cell Proliferation by Glycerol" Life Sci., 1991, 48(16): 1511-7.
Canadian Office Action dated Oct. 13, 2016; Application No. 2,780,536.
Extended European Search Report dated Oct. 21, 2016; Application No. 15196213.1.
Communication of a Notice of Opposition including exhibits EP Application No. 10000518.0 (Patent No. EP2228453) dated Sep. 12, 2017.
Communication Pursuant to Article 94 (3) EPC, Application No. 14750092.0, dated Dec. 22, 2017.
Canadian Office Action, Application No. 2,917,912, dated Jan. 9, 2018.
Communication of a Notice of Opposition including exhibits, EP Application No. 13706856.5 (U.S. Pat. No. 2,814,981) dated Apr. 4, 2018.
Communication of a notice of intervention including exhibits by Cenata GmbH, EP Application No. 10000518.0 (Patent No. EP2228453) dated Apr. 13, 2018.
Brief Communication to Opponent 1 and Opponent 2 dated May 29, 2018 and Reply including exhibits of patent proprietor to notice(s) of opposition dated Apr. 26, 2018, EP Application No. 10000518.0 (Patent No. EP2228453).
Brief Communication regarding letter from the opponent O2 (Cenata) of Jun. 6, 2018, including exhibits, EP Application No. 10000518.0 (Patent No. EP2228453), dated Jun. 14, 2018.
Antje Milde et al.: "Improved DNA typing of human urine by adding EDTA", Int. J Legal Med, Jan. 1, 1999, pp. 209-210, XP055291033.
Brown "Effect of Blood Collection and Processing on Radioimmunoassay Results for Apolipoprotein B in Plasma" Clinical Chemistry, 36/9. 1662-1666, 1990.
Butler "Genetics and Genomics of Core Short Tandem Repeat Loci Used in Human Identity Testing," Journal of Forensic Science, vol. 51, No. 2, pp. 253-265, Mar. 2006.
Cannas A, Kalunga G, Green C, Calvo L, Katemangwe P, Reither K, Perkins MD, Maboko L, Hoelscher M, Talbot EA, Mwaba P. Implications of storing urinary DNA from different populations for molecular analyses. PloS one. Sep. 10, 2009;4(9):e6985.
Cherepanova A, Tamkovich S, Pyshnyi D, Kharkova M, Vlassov V, Laktionov P. Immunochemical assay for deoxyribonuclease activity in body fluids. Journal of immunological methods. Aug. 31, 2007;325(1):96-103.
Co-pending U.S. Appl. No. 10/605,669, filed Oct. 16, 2003, published on Jul. 15, 2004 as 2004/0137417.
Co-pending U.S. Appl. No. 12/689,370, filed Jan. 19, 2010, Published as 2010/0184069 A1 on Jul. 22, 2010.
Co-pending U.S. Appl. No. 12/704,030, filed Feb. 11, 2010, Published as 2010/0209930 on Aug. 19, 2010.
Co-pending U.S. Appl. No. 12/850,269, filed Aug. 4, 2010, Published on Dec. 16, 2010 as 2010/0317107.
Co-pending U.S. Appl. No. 12/941,437, filed Nov. 8, 2010, Published as 2011 /0111410A1 on May 12, 2011.
Co-pending U.S. Appl. No. 13/766,207, filed. Feb. 13, 2013, Published on Mar. 20, 2014 as 2014/0080112.
Co-pending U.S. Appl. No. 14/071,969, filed Nov. 5, 2013, Published on Feb. 18, 2014 as 2014/00545508.
Co-pending U.S. Appl. No. 14/153,204, filed Jan. 13, 2014, Published on Jul. 7, 2014 as 2014/0199681.
Co-pending U.S. Appl. No. 14/907,167, filed Jan. 22, 2016, Published on Jun. 23, 2016 as 2016/0174544.
Co-pending U.S. Appl. No. 15/010,549, filed Jan. 29, 2016, Published on May 26, 2016 as 2016/0143268.
Costa et al. "Fetal Expressed Gene Analysis in maternal Blood: A New Tool for Noninvasive Study of the Fetus" Clinical Chemistry, vol. 49, No. 6, pp. 981-983, 2003.
Dean, (proceeding national Academy of Sciences (2002) vol. 99, pp. 5261-5266).
Decision to Refuse a European Patent Application dated May 3, 2007, Application No. 03 256 535.0-2113.
Fernando et al., "Stabilization of cell-free RNA in blood samples using a new collection device" Clinical Biochemistry, vol. 45, No. 16-17, pp. 1497-1502, dated Nov. 1, 2012.

(56) References Cited

OTHER PUBLICATIONS

Fernando et al., "Stabilization of Cell-Free RNA in Plasma for Noninvasive Diagnosis and Prognosis" URL:http://www.streck.com/resources/Cell_Stabilization/02_Paper_Cell-Free_RNA_BCT_Stabilization_of_Cell-Free_RNA_in_Plasma.pdf Retrieved on May 15, 2014.
Gielis, E.M.,"Cell-Free DNA: An Upcoming Biomarker in Transplantation," American Journal of Transplantation May 13, 2015.
Haaland, Arne. *Molecules and models: the molecular structures of main group element compounds*. Oxford University Press, 2008. (abstract available at http://www.oxfordscholarship.com/view/10.1093/acprof:oso/9780199235353.001.0001/acprof-9780199235353-chapter-12).
Kashiwasaki et al. "Influence of upper and lower thermoneitral room temperatures (20° C. and 25° C.) on fasting and post-prandial resting metabolism under different outdoor temperatures," European Journal of Clinical Nutrition, vol. 44, pp. 405-413, 1990.
Kelly, Brian N., "Circulating microRNA as a biomarker of human growth hormone administration to patients," Mar. 12, 2013, vol. 6, Issue 3.
Kreuzer et al.. "Highly Sensitive and specific Fluorescence Reverse Transcription—PCR Assay for the Psuedogene-free Detection of β-actin Transcripts as Quantitative Reference" Clinical Chemistry, vol. 45, No. 2, pp. 297-300, 1999.
Latifa El Bali et al.: "Comparative Study of Seven Commercial Kits for Human DNA Extraction from Urine Samples Suitable for DNA Biomarker-Based Public Health Studies", Journal of Biomolecular Techniques, Dec. 1, 2014.
May et al. "How Many Species Are There on Earth?," Science vol. 241 p. 1441-1449, 1988.
Miller "A Simple Salting Out Procedure for Extracting DNA from Human Nucleated Cells," Nucleic Acids Research vol. 16, p. 1215 (1988).
Modrek "Genome-wide Detection of Alternative Splicing in Expressed Sequences of Human Genes," Nucleic Acid Research, vol. 29, No. 13 pp. 2850-2859, (2001).
Nicole T Vu et al.: "Genotyping for DQA1 and PM loci in urine using PCR-based amplification: Effects of sample volume, storage temperature, preservatives, and aging on DNA extraction and typing", Forensic Science International., vol. 102, No. 1, May 1, 1999, pp. 23-34.
Passage from confidential document, Streck, Inc. Cell-Free DNA BCT 510(k) Premarket Notification, Sep. 19, 2012.
Rykova et al., "Concentrations of Circulating RNA from Healthy Donors and Cancer Patients Estimated by Different Method," Ann, N.Y. Acad. Sci. (2006) vol. 1075, pp. 328-333.
S.H. Zhang et al.: "Genotyping of urinary samples stored with EDTA for forensic applications", Genetics and Molecular Research, vol. 11, No. 3, May 10, 2012, pp. 3007-3012, XP055291026, DOI: 10.4238/2012.
Schatz et al.; "Presentation of Cell-Free DNA in Stored Blood Samples for the Analysis of the (M) Sep. 9 Colorectal Cancer Screening Marker Enables Sample Shipment by Mail", May 2011, Published as a poser at the conference on International federation of clinical chemistry and laboratory medicine Worldlab and EU, Berlin, Germany.
Skidmore et al., "Characterization and Use of the Potent Ribonuclease Inhibitor Aurintricarboxylic Acid for the Isolation of RNA from Animal Tissues," Biochem Journal, 263, pp. 73-80 (1989).
Slocum et al., "Electron-Microscopic Cytochemical Localization of Diamine and polyamine oxidases in Pea and Maize Tissues," Planta vol. 183, pp. 443-450, (1991).
Su YH, Wang M, Aiamkitsumrit B, Brenner DE, Block TM. Detection of a K-ras mutation in urine of patients with colorectal cancer. Cancer Biomarkers. Jan. 1, 2005;1(2, 3):177-82.
The Scientific Committee on Cosmetic Product and Non-Food Products intended for Consumers "Opinion Concerning the Determination of Certain Formaldehyde Releasers in Cosmetic Products" Dec. 22, 2002, pp. 1-9.
Tong YK, Lo YD. Diagnostic developments involving cell-free (circulating) nucleic acids. Clinica Chimica Acta. Jan. 31, 2006;363(1):187-96.
Hallick et al.; Use of Aurintricarboxylic Acid as in Inhibitor of Nucleases During Nucleic Acid Isolation; Nucleic Acid Research, (1977) vol. 4, pp. 3055-3064.
Smit et a; Semiautomated DNA Mutation Analysis Using a Robotic Workstation and Molecular Beacons; Clinical Chemistry, 2001, vol. 47, pp. 739-744.
What are the regulatory Definitions for "Ambient", "Room Temperature" and "Cold Chain" (https://www.gmp-compliance.org/gmp-news/what-are-the-regulatory-defintions-for-ambient-room-temperature-and-cold-chain) Feb. 3, 2017.
Wang and Enkel; Lipoprotient Lipase: from gene to obesity; Am J Physiol Endocrinol Met, 2009, vol. 297, pp. E271-E288.
Canadian Office Action, CA Application No. 2,938,275 dated May 13, 2019.
European Office Action, EP Application No. 13166264.5 dated Jan. 9, 2019.
Swarup et al; Circulating (cell-free) Nucleic Acids—A Promising, Non-Invasive Tool for Early Detection of Several Human Diseases; 2007; FEBS Letters 581, pp. 795-799.
Ames et al.; 1975, An Appraisal of the "Vacutainer" System for Blood Collection, Ann. Clin. Biochem, 12: 151-155.

\* cited by examiner

COMPOSITIONS AND METHODS FOR STABILIZING CIRCULATING TUMOR CELLS

FIELD OF THE INVENTION

The teachings herein relate to devices and methods for stabilizing and preserving circulating tumor cells without damaging the tumor cell integrity for improved protection and regulation of circulating tumor cells during collection, storage, and shipment.

BACKGROUND OF THE INVENTION

In the peripheral blood of patients with solid tumors of epithelial origin, studies have identified circulating cells that have characteristics of tumor cells. These cells that are present in the bloodstream of cancer patients (referred to as circulating tumor cells or CTCs) are thought to play an important role in cancer metastasis by breaking loose from a solid tumor, entering the circulation, and then migrating to distant organs to develop secondary tumors. As such, circulating tumor cell (CTC) enumeration and characterization in the blood of cancer patients is useful for cancer prognostic and treatment monitoring purposes. Even though the number of CTCs present in patient blood is very low, robust technologies have been developed to enumerate and characterize CTCs in patient blood samples. CTCs are detectable in the blood of patients with metastatic cancer using a number of different technologies. Since CTCs are rare they need to be enriched from patient blood for accurate enumeration and characterization. Most of the CTC enrichment and identification assays available today are based on enrichment with anti-EpCAM antibodies and subsequent identification using anti-cytokeratin antibodies. An example is the CellSearch® instrument system available from Janssen Diagnostics, Raritan, N.J.

While the presence of CTCs in patients with cancer has been known for over a century, utilization of these rare cells in cancer diagnosis and prognosis was not feasible since methodologies to detect, isolate and characterize CTCs have not been developed until recently. With the development of robust methodologies to enrich, isolate and characterize CTCs in different types of cancers that are found in solid organs, several clinical studies have been conducted to investigate the possible use of CTCs in cancer diagnosis and prognosis. Assays that enumerate CTCs using the Cell Search® system have been developed for use as an aid to monitor patients with metastatic breast, colorectal, and prostate cancers. It has also been shown the potential usefulness of CTC enumeration using the Cell Search™ system for monitoring patients with melanoma, urothelial, and lung cancer.

Factors that limit the utility of CTCs in cancer diagnosis and prognosis are the low abundance and the fragility of the CTCs that may introduce variability in the evaluation of CTCs using different assay platforms. Transportation of blood samples from the site of phlebotomy to another facility is commonly required for CTC enumeration and characterization. During post-phlebotomy blood sample transportation/storage, fragile CTCs may degrade and compromise the accuracy of CTC enumeration and characterization.

There is a growing interest in the use of CTCs in non-invasive diagnosis, prognosis and monitoring of treatment regimens. The low abundance of the CTCs and their fragile nature may introduce variability in the evaluation of CTCs using different assay platforms. This fragile nature of CTCs arises due to the apoptosis of CTCs which begins after separation from the tumor of origin and after removal of blood from a patient. Therefore, it is necessary to address several pre-analytical issues that arise during the time between blood draw and CTC enrichment and characterization in order to effectively preserve the CTCs for analysis. These include delays in blood processing, blood storage temperature, and agitation of the sample during transport and shipment of blood. Such conditions may affect the integrity of already fragile CTCs causing accurate enumeration and characterization of CTCs difficult. As a result, it is important to consider the type of blood collection device and post-phlebotomy conditions while working with CTC samples.

There is thus a need for methods of stabilizing and protecting circulating tumor cells whereby structural integrity is maintained so that shipping and storage is possible with minimal deleterious effect on the circulating tumor cells. There is a further need for such methods where the detrimental effects of aldehyde fixation are avoided.

SUMMARY OF THE INVENTION

The teachings herein employ a protocol using a unique protective agent composition that successfully preserves samples while stabilizing CTC integrity for a prolonged period (e.g., which may be at least 14 days, and which may be at room temperature). The present teachings provide a consistent and efficient method for preserving CTCs in biological samples. Data demonstrated herein describes a method that reduces cell lysis and nuclease activity, and also permits accurate and precise analytical analysis by virtue of the preservation of the final concentration of recoverable CTCs over time. In so doing, the teachings provide a novel approach that improves the downstream clinical analysis of CTCs. The present teachings describe protecting the CTCs by inhibiting all cellular metabolic activity in CTCs in blood. As a result of metabolic inhibition of OTCs in blood all apoptotic and necrotic pathways are inhibited and CTCs are protected from cell degradation. Therefore it is no longer necessary to isolate and characterize CTCs immediately after venipuncture. Furthermore, samples can be stored at room temperature for up to 14 days without deleterious effects to sample integrity, which eliminates the need for cold storage of the blood sample.

In one aspect, the present teachings contemplate a method for blood sample treatment comprising locating a protective agent into the blood collection devices described herein. The protective agent may include a preservative. A blood sample may be drawn into the blood collection device, the blood sample having a first CTC concentration. The blood collection device containing a blood sample may be transported from a first location to a second location, wherein at least a portion of the transporting occurs at a temperature of greater than about 0° C. The CTCs from the sample may be isolated at least 24 hours after blood draw, the sample having a second CTC concentration, wherein the second CTC concentration is not lower or higher than the first CTC concentration by any statistically significant value.

The teachings herein further include that the preservative may be selected from the group consisting of diazolidinyl urea and imidazolidinyl urea. The concentration of the preservative prior to the contacting step may be between about 0.1 g/ml and about 3 g/ml. The circulating tumor cells may be isolated from the sample at least 3 days after blood draw. The circulating tumor cells may be isolated from the sample at least 7 days after blood draw. The circulating tumor cells may be isolated from the sample at least 14 days after blood draw. The transporting step may occur without freezing the blood sample to a temperature colder than about −30° C. The protective agent may contact the circulating tumor cells so that after a period of at least 7 days from the time the blood sample is drawn, the amount of circulating tumor cells is at least about 90% of the amount of circulating tumor cells at the time the blood sample is drawn. The protective agent may contact the circulating tumor cells so that after a period of at least 7 days from the time the blood sample is drawn, the amount of circulating tumor cells present in the sample is about 100% of the amount of circulating tumor cells present in the sample at the time the blood sample is drawn.

The teachings herein contemplate improved protective agent compositions, and methods of stabilizing a biological sample for analysis. The protective agent compositions will generally include a preservative agent as described herein, and a quenching agent for substantially abating any free aldehyde (e.g., formaldehyde) from reacting with DNA within a sample. The protective agent composition may also include one or more nuclease inhibitors. The protective agent composition may also include one or more metabolic inhibitors. The methods described herein may comprise a step of obtaining in blood collection device a biological sample from a subject. The biological sample may include at least one circulating tumor cell from the subject. The methods may include a step of contacting the biological sample while within the blood collection device with a protective agent composition that includes a preservative agent, an optional anticoagulant, and a quenching agent to form a mixture that includes the protective agent composition and the sample. The methods may include a step of quenching any free formaldehyde that may be present with the quenching agent from the protective agent composition so that the free formaldehyde reacts to form a reaction product that is inert to the CTCs within the biological sample. The resulting mixture may be devoid of any aldehyde, and CTCs within the sample may be suitable for downstream applications.

For samples derived from blood, there may be a blood draw step of drawing blood from a patient into a blood collection device that has the protective agent composition loaded therein prior to the blood draw step. The method may include a step of transporting the sample while it is contacted with the protective agent composition from a blood draw site to a clinical laboratory (e.g., one located at least 100 meters, 1000 meters, 10,000 meters from the blood draw site) at which a sample analysis will occur. The quenching occurs prior to and/or substantially simultaneously with the contacting step. The methods may include a step of isolating circulating tumor cells from the sample. The methods may be free of any step of centrifugation of the sample. The methods may be free of any step of isolating cell-free fetal DNA, cell-free DNA, cell-free RNA or cellular RNA from a blood sample. The methods may be free of any step of refrigerating the sample (e.g., to a temperature below room temperature, such as about 10° C. or cooler) after it has been contacted with the protective agent composition.

As can be appreciated from the above, the teachings herein provide for advantageous treatment of CTC-containing samples and provide stabilized samples that are essentially free of detectable covalent modifications that inhibit downstream testing of the characteristics of CTCs.

DETAILED DESCRIPTION

Figure 1:
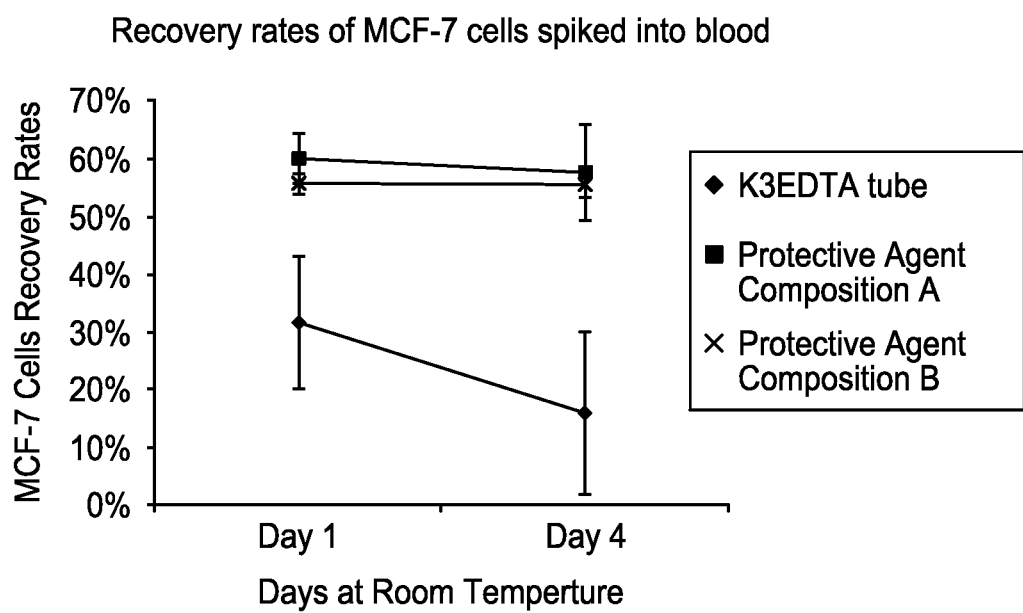
FIG. 1 shows a graph displaying the effect of two exemplary protective agent compositions and a standard $K_3EDTA$ composition on MCF-7 cell recovery at Day 1 and Day 4 post blood draw.

This application is related to and claims the benefit of the filing date of U.S. Provisional Application Ser. No. 61/857,847 filed Jul. 24, 2013, the contents of this application being hereby incorporated by reference for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Unless otherwise stated, percentages as set forth herein refer to percent by weight. Further, unless the context of the discussion makes clear to the contrary, references to circulating tumor cells refers not only to intact circulating tumor cells, but to tumor cell fragments.

The present teachings contemplate a non-invasive screening method for the identification of circulating tumor cells that are potentially indicative of cancer diagnosis and progression. The teachings herein envision not only preserving the state of any cells in a sample but also envisions protecting the circulating tumor cells from any adverse effects during any delay between sample collection and processing and/or testing. The methods of the teachings herein generally involve steps of contacting a biological sample (which may include multiple blood cells and cell-free biomolecules), with an aldehyde-free (e.g., formaldehyde-free) protective agent composition in an amount and time that is sufficient to prevent degradation of the circulating tumor cells. The treatment is such that it substantially prevents any free aldehyde from adversely reacting with the CTCs of the sample such as by employing a quenching agent. In this manner, substantial quantities of CTCs can be maintained within and isolated from the sample. The CTC integrity is substantially preserved in its as provided state (e.g., the state at the time of blood draw) by avoiding the damaging effects of any aldehyde (e.g., formaldehyde). Thus, accurate and precise analytical analysis of the CTCs of the sample can be achieved. The method may further include steps of analyzing the CTCs from a sample that has been treated in accordance with the above, or that have otherwise been contacted with the protective agent composition and the quenching agent therein. As noted, the teachings herein permit identification of CTC characteristics for prognostic and diagnostic use of various pathological conditions in the clinic.

Protective Agent Compositions A & B as described in the examples below and shown in the drawings include a formaldehyde free stabilization reagent that stabilizes CTCs in a blood sample for up to 14 days at room temperature. They do so by inhibiting cell metabolism in CTCs in blood and preventing cellular apoptosis and necrosis that degrade the CTCs in blood. These examples were designed to investigate the effectiveness of this blood collection devices for the stabilization of CTCs in a blood sample for an extended period of time at room temperature.

The study was approved by the institutional review board of the Methodist Hospital, Omaha, Nebr., USA and informed consent was obtained from all donors prior to blood draw. Blood specimens were collected from apparently healthy adult donors by standard phlebotomy techniques.

Breast cancer cell line, MCF-7 cells was obtained from American Type Culture Collection (Rockville, Md., USA) and routinely passaged in Eagle's MEM medium containing 10% fetal bovine serum at 37° C. in humidified atmosphere of 5% $CO_2$.

For the MCF-7 cell spiking experiment, blood from each healthy donor (7 donors in total) was drawn into 10 mL $K_3$EDTA tubes (BD Vacutainer®, Becton Dickinson, Franklin Lakes, N.J., USA), and 10 mL tubes containing Protective Agent A and 10 mL tubes containing Protective Agent B. The blood volume was as close to 10 mL as possible for all tube types. MCF-7 cells (2000 cells/10 mL blood) were then spiked into all tubes and blood was mixed immediately after spiking by inverting 10 times each. All samples were shipped at ambient temperature to Geneuity Clinical Research Services (Maryville, Tenn., USA) and analyzed on the CellSearch system on days 1 and 4 post phlebotomy to determine the stability of spiked MCF-7 cells. Blood samples were maintained at room temperature during the entire process.

While the CellSearch system was utilized for the examples herein, it is envisioned that the protective agent compositions described herein could be utilized with any device and/or platform equipped for tumor cell enrichment and characterization.

Examples

Blood was drawn from each donor into multiple 10 mL $K_3$EDTA tubes and multiple 10 mL tubes for each of Protective Agent. Compositions A & B. All tube types were spiked with MCF-7 breast cancer cells and stored at room temperature. Spiked MCF-7 cells were enumerated using the CellSearch™ system on days 1 and 4. Effect of storage on the stability of proteins and nucleic acids in MCF-7 cells isolated from $K_2$EDTA tube and Protective Agent Compositions A & B was determined using fluorescent staining and confocal laser scanning microscopy.

Overall, enumeration of MCF-7 cells in $K_2$EDTA blood showed a significant drop in recovered MCF-7 cells at day 1 and 4 compared to values obtained for Protective Agent Compositions A & B. However, in blood drawn into tubes containing Protective Agent Compositions A & B, MCF-7 cell count was stable up to 4 days at room temperature. Epithelial cell adhesion molecule (EpCAM) and cytokeratin (CK) in MCF-7 cells isolated from tubes containing Protective Agent Compositions A & B were stable at room temperature for up to 4 days, whereas in MCF-7 cells isolated from $K_3$EDTA blood showed reduced EpCAM and CK protein expression. The CK protein expression showed no significant change over 4 days in tubes containing Protective Agent Compositions A & B. Similarly, Protective Agent Composition A showed improved stabilizing of c-fos mRNA as compared to $K_3$EDTA tubes. No significant change in cyclin D1 mRNA expression was observed in all tubes.

As further discussed in the details below, Protective Agent Compositions A & B provide preservation and stabilization of CTCs in blood samples for at least 4 days at room temperature. In doing so, it facilitates the development of new non-invasive diagnostic and prognostic methodologies for CTC enumeration as well as characterization.

Figure 2:
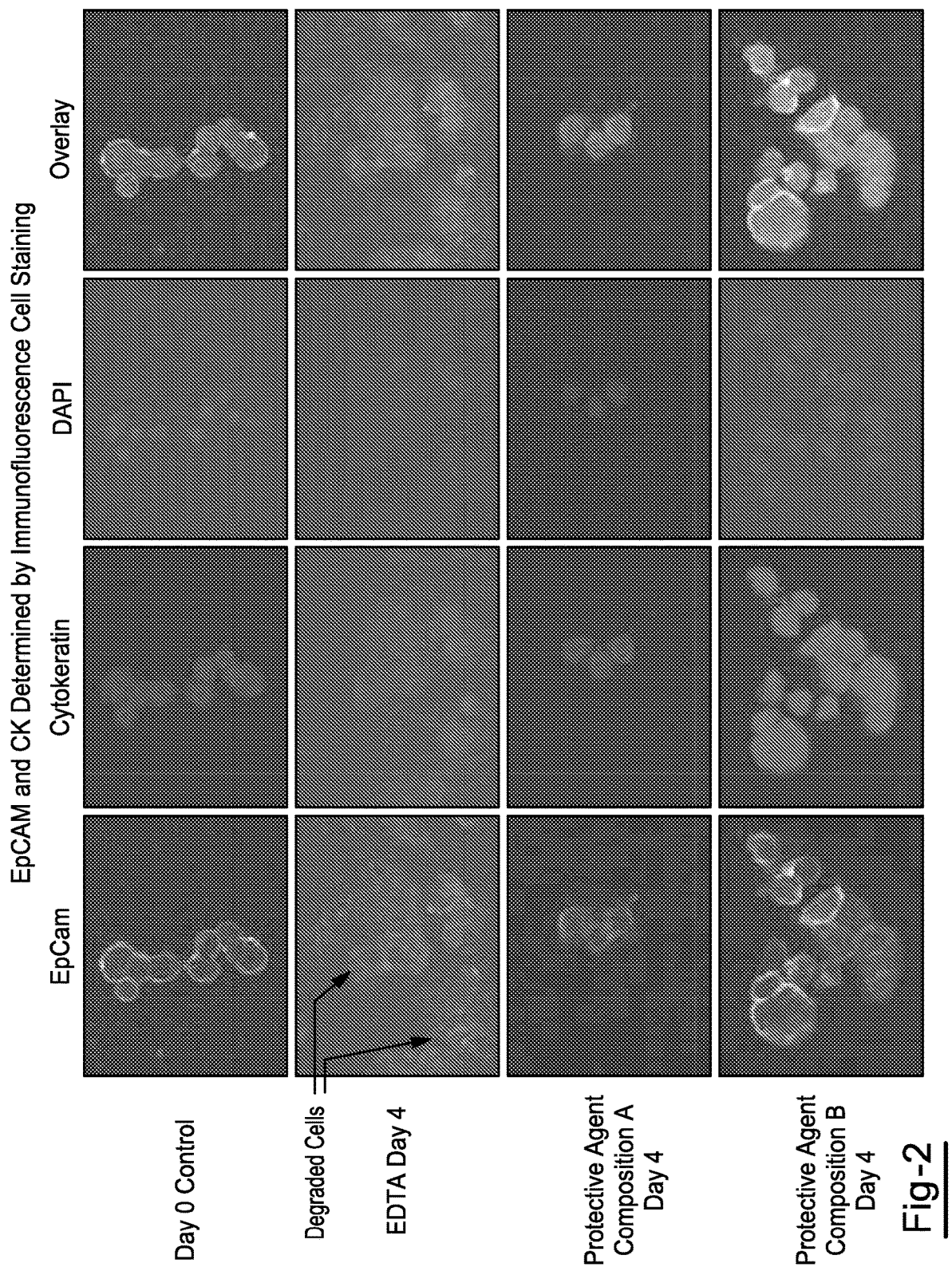
FIG. 2 shows immunofluorescence cell staining results (EpCAM and Cytokeratin) of two exemplary protective agent compositions and a standard $K_3EDTA$ composition.

Effect of Storage on the Stability of EpCAM and CK Determined by Immunofluorescence Cell Staining—FIG. 2

Blood was drawn from each donor into one 10 mL $K_3$EDTA tube, one 10 mL tube containing Protective Agent Composition A, and one 10 mL tube containing Protective Agent Composition B. Plasma was separated from blood within 2 h post collection. To separate plasma, blood samples were centrifuged at 300×g for 20 min at room temperature. The upper plasma layer was carefully removed without disturbing the buffy coat and transferred to a new tube that was then centrifuged at 5000×g for 10 min. The cell-free plasma was then spiked with MCF-7 cells 2,000 cells/4-5 mL of plasma) and stored at room temperature. On days 0 and 4, MCF-7 cells were washed with phosphate buffered saline solution and centrifuged at 500 rpm for 7 minutes on glass slides using Shandon Cytospin® 3 cytocentrifuge. Slides were then dried and immunostaining for EpCAM and Cytokeratin were carried out with a primary antibody cocktail containing a mouse anti-EpCAM antibody (VU-1D9, # sc-51681, 1:1:100) and a mouse anti-CK antibody (T-13, # sc-241376, 1:100). After 1 h of incubation, slides were washed twice with PBS and probed with fluorescent labeled secondary antibodies for mouse anti-EpCAM (donkey anti-mouse IgG-FITC, # sc-2099, 1:200) and mouse anti-CK (donkey anti-goat IgG-PerCP-Cy5.5, # sc-45102, 1:200) antibodies for 1 h. After washing slides twice with PBS, coverslips were mounted onto slides with UltraCruz™ mounting medium (# sc-24941) containing 4', 6-diamidino-2-phenylindole (DAPI) to counterstain cell nuclei. All antibodies and mounting medium were purchased from Santa Cruz Biotechnology, Inc. (Dallas, Tex., USA) and manufacturer's protocol was followed. Fluorescent images were obtained using Zeiss LSM 510 META NLO laser scanning confocal microscope (Oberkochen, Germany).

Figure 3:
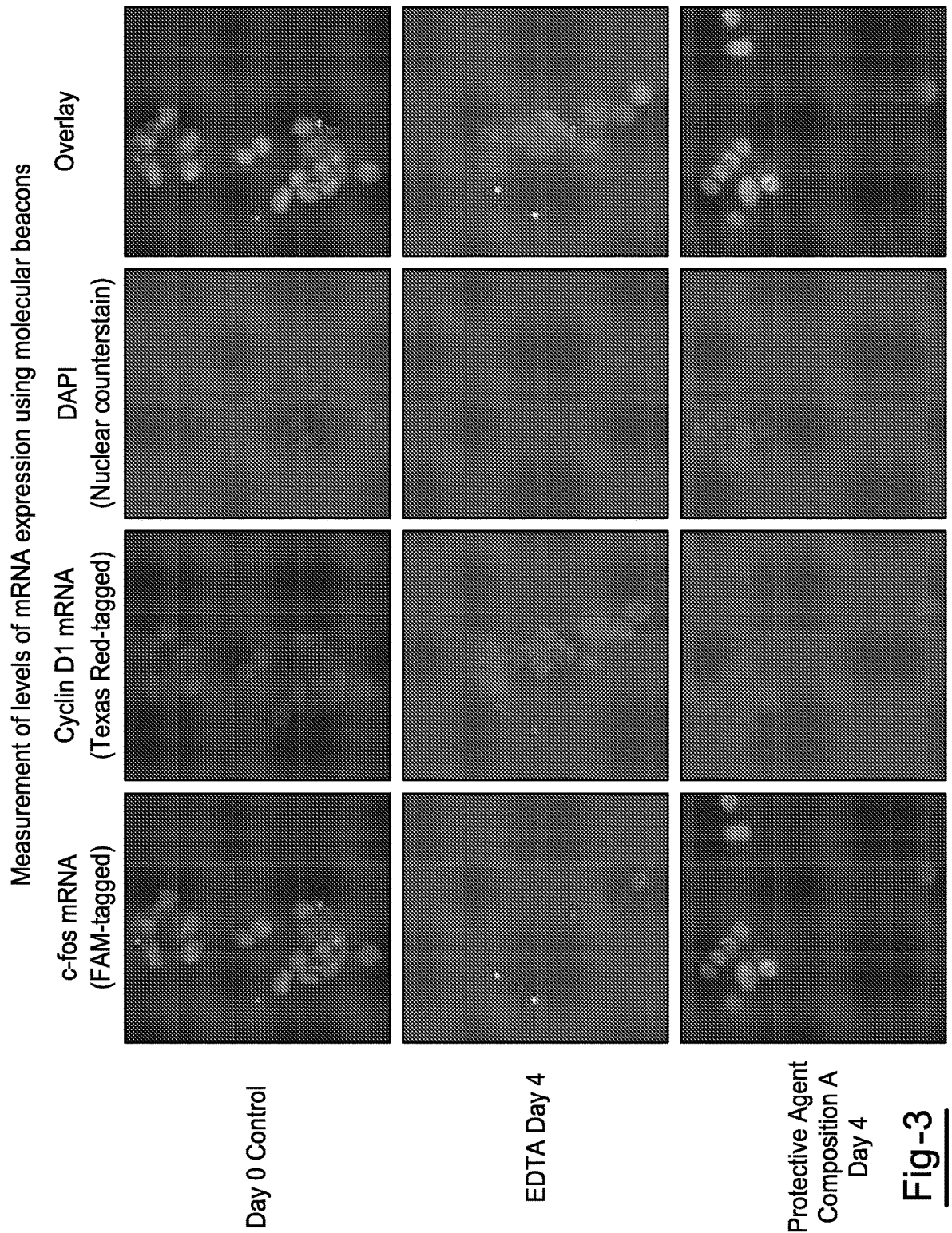
FIG. 3 shows fluorescence cell staining results showing levels of mRNA expression after contact with one exemplary protective agent composition and a standard $K_3EDTA$ composition.

Effect of Storage on the Stability of mRNA Molecules Using Molecular Beacons—FIG. 3

Cytospin slides of spiked MCF-7 cells were prepared as described above. Cells on the slides were treated with ice cold methanol (−10° C.) for 5 to 10 min. After air drying, the slides were stained with a mixture of 200 nmol/L of fluorescent-tagged molecular beacons targeting c-fos or cyclin D1 mRNAs in Opti-MEM (Invitrogen) at 37° C. for 1 h. Stained cells on the slides were then washed, counterstained with DAPI and examined using a confocal microscope. The molecular beacons were purchased from Eurofins MWG Operon (Huntsville, Ala.).

Stability of Spiked MCF-7 Cells in Blood FIG. 1

Experiments were carried out to determine the ability of Protective Agent Compositions A & B to stabilize CTCs during blood sample storage and transportation as compared to regular $K_3$EDTA blood collection tubes. Parallel blood samples drawn into K$_3$EDTA and tubes containing Protective Agent Compositions A & B and spiked with MCF-7 cells were analyzed using the CellSearch system for spiked tumor cell recovery. As shown in FIG. 1, Protective Agent Compositions A & B demonstrated desired percentage recovery of the tumor cells at room temperature for up to 4 days. In Protective Agent Compositions A & B, at day 1, 60% (Standard deviation (SD)=4%, coefficient of variation (CV)=7.3%) of spiked MCF-7 cells were recovered and at day 4 it was 58% (SD=8%, CV=14.3%). In contrast, K$_3$EDTA tubes failed to preserve CTCs resulting in a much lower recovery rates for both day 1 and 4 as compared to Protective Agent Compositions A & B. In K$_3$EDTA tubes, at day 1, recovery rate was 32% (SD 12%, CV=36.3%) of the spiked MCF-7 cells and at day 4 it was 16% (SD=14%, CV=87%).

Effect of Storage on the Stability of EpCAM and CK Proteins Determined by Immune Fluorescence Cell Staining—FIG. 2

FIG. 2 illustrates the effects of room temperature storage on the stability of tumor-associated transmembrane protein EpCAM and cytoskeleton protein cytokeratin of MCF-7 tumor cells spiked into blood plasma. According to FIG. 2, EpCAM protein which is expressed on the cell membrane of MCF-7 cells are stable up to 4 days at, room temperature in tubes containing Protective Agent Compositions A & B whereas in K$_3$EDTA tubes this membrane protein was partially degraded by day 4. According to FIG. 2, fluorescence signal for EpCAM cell membrane protein is very weak and diffused in MCF-7 cells spiked into K$_3$EDTA blood at day 4, CK protein is stabilized in tubes containing Protective Agent Compositions A & B at day 4, however this protein was less stable in K$_3$EDTA tubes at day 4 as evidenced from reduced fluorescence intensity for this protein in spiked MCF-7 cells recovered from K$_3$EDTA tubes. Staining of cells with DAPI shows that nucleus and nuclear content is stable in cells recovered from tubes containing Protective Agent. Compositions A & B but not from cells recovered from K$_3$EDTA tubes after 4 days of storage at room temperature (FIG. 2).

Effect of Storage on the Stability of mRNA Molecules Using Molecular Beacons—FIG. 3

Experiments were carried out to study the stability of mRNA in spiked MCF-7 cells recovered from Protective Agent Composition A and K$_3$EDTA tubes. Cytospins of recovered MCF-7 cells were prepared as described above. To detect mRNA in situ, fluorescent-labeled molecular beacons and a scanning confocal microscope was used. As shown in FIG. 3, c-fos mRNA (green fluorescence) and cyclin D1 mRNA (red fluorescence) were both stable in Protective Agent Composition A up to 4 days at room temperature. However in K$_3$EDTA tubes c-fos mRNA was not stable after 4 days of storage at room temperature, indicating that c-fos mRNA expression was significantly degraded or downregulated. The change in cyclin D1 mRNA level in MCF-7 cells recovered from KEDAT tube was minimal after 4 days incubation at room temperature.

In the example with results shown at FIG. 1, 2000 MCF-7 cells were spiked into each K$_3$EDTA tube and tubes containing Protective Agent Compositions A & B and shipped from Omaha Nebr. to Maryville, Tenn. by overnight shipping for analysis by the CellSearch™ System. Thus, this example represents a combination of transportation as well as storage effect on CTCs in blood samples. As shown in FIG. 1, our CTC recovery study conducted using spiked MCF-7 cells and analyzed by CellSearch™ System provided evidence that Protective Agent Compositions A & B are able to preserve CTCs during transportation and storage at room temperature for up to 4 days. Previous studies using CellSearch™ System have shown that the recovery rate for MCF-7 cells shortly after blood draw is between 62-89%, Our results show that in tubes containing Protective Agent Compositions A & B, post shipping day 1 and day 4 recovery rates of 61% and 57% respectively. There was no statistically significant difference between these two values indicating that CTCs are stable in Protective Agent Compositions A & B for 4 days after shipping at room temperature. However in K$_3$EDTA tubes, CTC recovery rate was very low compared to Protective Agent Compositions A & B. In K$_3$EDTA tubes post shipping day 1 and day 4 recovery rates were 32% and 16% respectively. There was a statistically significant decrease in CTC recovery in K$_3$EDTA tube at day 1 and day 4 compared to Protective Agent. Compositions A & B. As shown in FIG. 2, immunofluorescence staining of recovered CTCs for EpCAM and CK showed stability of these proteins in CTCs recovered from Protective Agent Compositions A & B 4 days after storage at room temperature. However cells recovered from K$_3$EDTA tubes showed degrading EpCAM and CK proteins after 4 days at the same temperature. DAPI staining of cells showed stable nucleus and nuclear content in CTCs recovered from Protective Agent Compositions A & B whereas CTCs recovered from K$_3$EDTA tubes showed degrading nucleus and nuclear content (FIG. 2).

The molecular beacon example shows that both c-fos and cycling D1 mRNA are stable in Protective Agent Composition A at room for up to 4 days (FIG. 3). However, CTCs recovered from K$_3$EDTA tubes showed CTCs with degrading c-fos and cyclin D1 mRNAs as shown in FIG. 3.

Analysis of the stabilizing reagent present in Protective Agent Compositions A & B by $^{13}$C-NMR has shown that the reagent is free of formaldehyde. Aldehyde based chemicals traditionally used in cell stabilization, such as formaldehyde and glutaraldehyde, are known to damage DNA and RNA by causing chemical modifications in nucleic acids and making nucleic acid-protein cross-links which make extraction of nucleic acids difficult. Application of such aldehyde based chemicals for CTC stabilization may cause problems for CTC characterization studies. Cell stabilizing reagent present in Protective Agent Compositions A & B have an advantage over aldehyde based stabilizing agents because of it has no negative effect on either nucleic acid extraction or amplification by PCR.

In these examples, Protective Agent Compositions A & B provide preservation and stabilization of CTCs in blood samples for up to 4 days at room temperature. In doing so, the protective agent compositions support the development of new non-invasive diagnostic and prognostic methodologies for CTC enumeration as well as characterization.

The teachings herein envision that a single protective agent composition may be employed that includes a preservative composition and a quenching agent. Such protective agent composition may be preloaded into a sample collection device, such as a blood collection tube (which may be evacuated to a pressure below atmospheric pressure after loading). Thus, it is possible that a sample may be taken from a subject directly into the sample collection device (e.g., a blood collection tube), at which time it will be contacted with the protective agent composition. It is also possible that a sample can be taken from a subject into a first container and the sample subsequently transferred to one or more second containers in which the protective agent composition is present.

The aldehyde-free (e.g., formaldehyde-free) protective agent composition may include a preservative composition such as one selected from the group consisting of: diazolidinyl urea, imidazolidinyl urea, dimethoylol-5,5-dimethylhydantoin, diethyl urea, 2-bromo-2-nitropropane-1,3-diol, oxazolidines, sodium hydroxymethyl glycinate, 5-hydroxymethoxymethyl-1-laza-3,7-dioxabicyclo [3.3.0] octane, 5-hydroxymethyl-1-laza-3,7-dioxabicyclo [3.3.0] octane, 5-hydroxypoly[methyleneoxy]methyl-1-laza-3,7-dioxabicyclo [3.3.0] octane, quaternary adamantine and any combination thereof. Though the aldehyde-free (e.g., formaldehyde-free) protective agent composition may release an aldehyde (e.g., formaldehyde), the teachings herein envision a specific step of quenching the aldehyde to render it inert to the CTCs.

The preservative composition is desirably used in combination with a quenching agent for helping to assure that nucleic acid (e.g., DNA) in the sample avoids being subjected to free aldehyde (e.g., free formaldehyde) which may cause one or more deleterious effects upon the nucleic acid. Accordingly, the teachings herein contemplate the use of at least one aldehyde quenching agent, which is employed in an amount and in a manner sufficient so that any free aldehyde (e.g., formaldehyde) released from the protective agent composition reacts to form a reaction product that is inert to the nucleic acid of the biological sample. Further, the resulting mixture is preferably devoid of any aldehyde, and nucleic acids within the sample are suitable for polymerase chain reaction and DNA sequencing, and will exhibit structural integrity comparable to native nucleic acids (e.g., DNA will exhibit ellipticity that is substantially similar that of untreated native DNA, as measured by circular dichroism spectroscopy or will exhibit DNA-dye fluorescence that is substantially similar to that of untreated native DNA, as measured by fluorescence spectroscopy).

The concentration of the preservative composition after sample contact may be greater than about 20 mg/ml, 10 mg/ml, 5 mg/ml, 2 mg/ml, less than about 0.8 g/ml of the mixture of protective agent composition and biological (e.g., blood) sample. The concentration of the preservative composition after sample contact may be more than about 0.1 g/ml of the mixture of protective agent composition and biological (e.g., blood) sample. By way of example, the concentration of the preservative composition after sample contact may be between approximately 0.1 g/ml to approximately 0.8 g/ml of the mixture of protective agent composition and biological (e.g., blood) sample. The concentration of the preservative composition after sample contact may be between approximately 0.3 g/ml to approximately 0.6 g/ml of the mixture of protective agent composition and biological (e.g., blood) sample. The concentration of the preservative composition both before and after contact with a blood sample may be modified depending upon what diagnostic procedures a sample may undergo. As an example, the concentration may be modified in the event that a sample is to undergo flow cytometry analysis. More specifically, the concentration may be increased in the event that a sample is to undergo flow cytometry analysis. Thus, the concentration of the preservative composition after sample contact may be greater than about 15 mg/ml, greater than about 25 mg/ml, or even greater than about 30 mg/ml after sample contact. The formulation of the protective agent composition (and the preservative composition contained therein) may also be modified such that a sample that will undergo flow cytometry analysis may contain diazolidinyl urea. The protective agent composition may also include a quenching agent. The protective agent composition may also include one or more metabolic inhibitors, one or more nuclease inhibitors and EDTA.

The quenching agent may be one or more compounds that include at least one functional group capable of reacting with an electron deficient functional group of an aldehyde (e.g., an amine compound that reacts with formaldehyde to form methylol and/or imine Schiff base or a cis-diol compound that reacts with formaldehyde to form a cyclic acetal). The quenching agent may be selected from amino acids, alkyl amines, polyamines, primary amines, secondary amines, ammonium salts, nucleobases or any combination thereof. The quenching agent may be selected from glycine, lysine, ethylene diamine, arginine, urea, adinine, guanine, cytosine, thymine, spermidine, or any combination thereof.

The concentration of the quenching agent is an amount that is sufficiently large that after contacting the sample with the protective agent composition, there is an absence of free aldehyde (e.g., an absence of free formaldehyde). However, the concentration is sufficiently small that dilution of the sample will not materially impact any analyzed characteristic of the sample. The concentration of the formaldehyde-quenching reagent after the sample contacting step may be above about 0.001 g/ml, 0.002 g/ml or even about 0.004 ml of the mixture of protective agent composition and biological (e.g., blood) sample. The concentration of the formaldehyde-quenching reagent after the sample contacting step may be below about 0.03 g/ml, 0.01 g/ml, or even about 0.008 g/ml of the mixture of protective agent composition and biological (e.g., blood) sample. By way of example, the concentration of the formaldehyde-quenching reagent after the sample contacting step may be between about 0.004 g/ml to about 0.008 g/ml.

Upon being brought into contact with a sample to form a mixture of the sample and protective agent composition (e.g., at time of a blood draw into a blood collection device containing a protective agent composition of the teachings herein), the protective agent composition may be present in an overall small fraction of the mixture volume. For example, it may be present in an amount that is less than about 5%, 2%, 0.5% or even less than about 0.3% of the overall mixture volume. For example, the protective agent composition may be present in an amount of from about 1:20 parts by volume to about 1:300 parts by volume of the mixture. The amount of the protective agent composition may be present from about 1:50 parts by volume to about 1:200 parts by volume of the mixture.

During at least the contacting step, the amount of the protective agent composition is present from about 1:20 (1 part protective agent composition to 20 parts total mixture) parts by volume to about 1:300 parts by volume of the total mixture (which includes both the protective agent composition and the biological sample). For instance, during at least the contacting step, the amount of the protective agent composition is present from about 1:100 parts by volume to about 1:200 parts by volume of the mixture.

The protective agent composition may include at least one preservative composition selected from diazolidinyl urea, imidazolidinyl urea, dimethoylol-5,5-dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo[3.3.0]octane, 5-hydroxymethyl-1-1aza-3,7dioxabicyclo[3.3.0] octane, 5-hydroxypoly[methyleneoxy]methyl-1-1aza-3,7dioxabicyclo[3.3.0]octane, quaternary adamantine, 2-aminoacetic acid or any combination thereof. By way of illustration, the contacting step may include employing as the protective agent composition, a composition that includes imidazolidinyl urea in an amount of about 0.1 to about 2.0% by weight of the total mixture of the protective agent composition plus a biological sample; optionally, ethylenediaminetetraacetic acid (EDTA) in an amount of about 0.05 to about 0.75% by weight of the total mixture of the protective agent composition plus a biological sample; and a quenching agent in an amount sufficient to react with any free aldehyde (e.g., formaldehyde) that may arise from the imidazolidinyl urea to form a reaction product that will not react to denature any protein of the biological sample. The protective agent composition (prior to contact with any biological sample) may include from about 20% to about 60% by weight imidazolidinyl urea. The protective agent composition may include at least about 30% by weight imidazolidinyl urea. The protective agent composition may include at least about 40% by weight imidazolidinyl urea and less than about 55% by weight imidazolidinyl urea. The protective agent composition may include from about 1% to about 10% by weight of the quenching agent. The protective agent composition may include at least about 2% by weight of the quenching agent. The protective agent composition may include at least about 4% by weight of the quenching agent and less than about 8% by weight of the quenching agent. The protective agent composition may include from about 1% to about 20% by weight EDTA. The protective agent composition may include at least about 5% by weight EDTA. The protective agent composition may include at least about 7% by weight EDTA and less than about 10% by weight EDTA.

The protective agent composition may be pre-loaded into a tube and may be pre-loaded in amount of from about 50 to about 400 µl of protective agent composition. The pre-loaded amount may be at least about 100 µl and less than about 300 µl. The pre-loaded amount may be at least about 150 µl and less than about 2500. Within the pre-loaded protective agent composition, the protective agent composition may comprise at least about 80 mg and less than about 100 mg of the protective agent composition. The quenching agent may comprise at least about 1 mg and less than about 15 mg of the protective agent composition. EDTA may comprise at least about 10 mg and less than about 25 mg of the protective agent composition. For the protective agent composition, it may include an amount of about 10 parts by weight of the protective agent composition per about 1 parts by weight of the quenching agent. The quenching agent may include a compound that includes at least one functional group capable of reacting with an electron deficient functional group of formaldehyde (e.g., an amine compound that reacts with formaldehyde to form methylol or imine Schiff base or a cis-diol compound that reacts with formaldehyde to form a cyclic acetal). The quenching agent may be an ingredient selected from amino acids, alkyl amines, polyamines, primary amines, secondary amines, ammonium salts, or a combination thereof, it may be an ingredient selected from glycine, lysine, ethylene diamine, arginine, urea, adinine, guanine, cytosine, thymine, spermidine, or any combination thereof. It may be an ingredient selected from glycine, lysine, ethylene diamine, urea or any combination thereof. The quenching step may include reacting any free aldehyde (e.g., formaldehyde) for forming a methylol, imine Schiff base, a Schiff base-quencher crosslink reaction product, a Schiff base dimer, or any combination thereof.

The protective agent may include one or more preservative agents, one or more nuclease inhibitors, one or more metabolic inhibitors, or any combination thereof. The one or more nuclease inhibitors may be selected from the group consisting of: diethyl pyrocarbonate, ethanol, aurintricarboxylic acid (ATA), glyceraldehydes, sodium fluoride, ethylenediamine tetraacetic acid (EDTA), formamide, vanadyl-ribonucleoside complexes, macaloid, heparin, hydroxylamine-oxygen-cupric ion, bentonite, ammonium sulfate, dithiothreitol (DTT), beta-mercaptoethanol, cysteine, dithioerythritol, tris (2-carboxyethyl) phosphene hydrochloride, a divalent cation such as $Mg^{+2}$, $Zn^{+2}$, $Fe^{+2}$, $Ca^{+2}$, $Cu^{+2}$ and any combination thereof. The one or more metabolic inhibitors may be selected from the group consisting of: glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof.

The amount of any active ingredient within the protective agent may generally be at least about 0.01% by weight. The amount of any active ingredient within the protective agent may generally be less than about 70% by weight. The protective agent may comprise at least about 10% diazolidinyl urea. The protective agent may comprise less than about 40% diazolidinyl urea. The protective agent may further contain at least about 1% of one or more enzyme inhibitors (e.g., nuclease inhibitors) such as EDTA and ATA. The protective agent may contain less than about 30% of one or more enzyme inhibitors. The protective agent may also contain at least about 1% of one or more metabolic inhibitors. The protective agent may contain less than about 20% of one or more metabolic inhibitors.

The protective agent composition optionally may include a nuclease inhibitor selected from the group consisting of: diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol (BME), cysteine, dithioerythritol, tris(2-carboxyethyl) phosphene hydrochloride, a divalent cation such as $Mg^{2+}$, $Mn^{2+}$, $Zn^{2+}$, $Fe^{2+}$, $Ca^{2+}$, $Cu^{2+}$, and any combination thereof. The protective agent composition may include a preservative composition, an aldehyde quenching agent, and an anticoagulant. In one preferred embodiment, the protective agent composition may include imidazolidinyl urea, glycine, and ethylenediamine tetraacetic acid.

The teachings herein contemplate applications including but not limited to extracting circulating tumor cells for use in detecting cancer (including but not limited to carcinomas, leukemia, and/or lymphoma). For instance, the teachings herein may be employed for detecting abnormal methylation for breast cancer, prostate cancer, gastric cancer, ovarian, colorectal cancer, bladder cancer, testicular cancer, esophageal cancer, melanoma or other cancers.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not only with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description. As to all of the foregoing general teachings, as used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight and vice versa. Thus, an expression in the Detailed Description of the Invention of a range in terms of at "x" parts by weight of the resulting polymeric blend composition "also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Concentrations of ingredients identified in Tables herein may vary ±10%, or even 20% or more and remain within the teachings.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or 'one' to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

Even if not expressly stated, teachings from a description of one embodiment may be combined with teachings for other embodiments unless the description makes clear that such embodiments are mutually exclusive, or that the resulting combination would be clearly inoperative in the absence of unreasonable experimentation.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A method for blood sample treatment comprising:
locating a protective agent into a tube, the protective agent including imidazolidinyl urea ("IDU"), glycince, and EDTA;
drawing the blood sample having a first circulating tumor cell concentration into the tube, whereby the blood sample contacts the protective agent;
isolating circulating tumor cells from the blood sample after the blood draw, the contacted blood sample having a second circulating tumor cell concentration, wherein the second circulating tumor cell concentration is not lower or higher than the first circulating tumor cell concentration by any statistically significant value; and
wherein a concentration of the IDU prior to the contacting step is between about 0.1 g/mL and about 3 g/mL;
wherein a concentration of the protective agent after the contacting step is less than about 0.8 g/mL; and
wherein a concentration of the glycine after the contacting step is below about 0.03 g/mL.

2. The method of claim 1, wherein the circulating tumor cells are isolated from the contacted blood sample at least 1 day after the blood draw.

3. The method of claim 1, wherein the circulating tumor cells are isolated from the contacted blood sample at least 3 days after the blood draw.

4. The method of claim 1, wherein the circulating tumor cells are isolated from the contacted blood sample at least 7 days after the blood draw.

5. The method of claim 1, wherein the circulating tumor cells are isolated from the contacted blood sample at least 14 days after the blood draw.

6. The method of claim 2, wherein the protective agent contacts the circulating tumor cells so that after a period of at least 7 days from a time the blood sample is drawn, an amount of the circulating tumor cells present in the contacted blood sample is at least about 90% of an amount of the circulating tumor cells at a time the blood sample is drawn.

7. The method of claim 2, wherein the protective agent contacts the circulating tumor cells so that after a period of at least 7 days from a time the blood sample is drawn, an amount of the circulating tumor cells present in the contacted blood sample is about 100% of an amount of the circulating tumor cells present in the blood sample at a time the blood sample is drawn.

8. The method of claim 1, wherein there is no significant degradation of EpCAM proteins in the contacted blood sample after 4 days at room temperature.

9. The method of claim 1, wherein there is no significant degradation of CK proteins in the contacted blood sample after 4 days at room temperature.

10. The method of claim 2, wherein at least 50% of the circulating tumor cells are recovered for isolation after day 1.

11. The method of claim 2, wherein at least 50% of the circulating tumor cells are recovered for isolation after day 4.

12. The method of claim 10, wherein CK protein in the contacted blood sample is stabilized.

13. The method of claim 10, wherein EpCAM protein in the contacted blood sample is stabilized.

14. The method of claim 1, wherein c-fos mRNA in the circulating tumor cells remains stable after 4 days at room temperature.

15. The method of claim 2, wherein DNA present in the contacted blood samples exhibits ellipticity that is substantially similar to that of untreated native DNA as measured by circular dichroism spectroscopy.

16. The method of claim 10, wherein DNA present in the contacted blood samples exhibits DNA-dye fluorescence that is substantially similar to that of untreated native DNA as measured by fluorescence spectroscopy.

17. The method of claim 1, wherein the protective agent includes beta-mercaptoethanol.

18. The method of claim 1, wherein the concentration of the protective agent after the contacting step is between about 0.1 g/mL to about 0.8 g/mL.

* * * * *

UNITED STATES PATENT AND TRADEMARK OFFICE
CERTIFICATE OF CORRECTION

PATENT NO. : 10,674,721 B2
APPLICATION NO. : 16/153273
DATED : June 9, 2020
INVENTOR(S) : Rohan M. Fernando et al.

Page 1 of 1

It is certified that error appears in the above-identified patent and that said Letters Patent is hereby corrected as shown below:

In the Claims

Column 14, Lines 28 and 29, In Claim 1, delete "glycince, and EDTA;" and insert --glycine, and EDTA;--

Signed and Sealed this
Twenty-second Day of September, 2020

Andrei Iancu
*Director of the United States Patent and Trademark Office*